United States Patent
Abu Nassar et al.

(10) Patent No.: US 7,493,178 B2
(45) Date of Patent: Feb. 17, 2009

(54) ELECTRODE POSITIONING DEVICE FOR THREE-AXES INDEPENDENT ELECTRODE POSITIONING

(75) Inventors: Nabil J. Abu Nassar, Nzareth (IL); Maroon J. Abu Nassar, Nzareth (IL)

(73) Assignee: Nan Instruments Ltd., Yokneam (Industrial Park) (IL)

( * ) Notice: Subject to any disclaimer, the term of this patent is extended or adjusted under 35 U.S.C. 154(b) by 152 days.

(21) Appl. No.: 10/525,097

(22) PCT Filed: Aug. 17, 2003

(86) PCT No.: PCT/IL03/00679

§ 371 (c)(1),
(2), (4) Date: Feb. 16, 2006

(87) PCT Pub. No.: WO2004/017148

PCT Pub. Date: Feb. 26, 2004

(65) Prior Publication Data

US 2006/0223408 A1    Oct. 5, 2006

(30) Foreign Application Priority Data

Aug. 18, 2002 (IL) .................................... 151315

(51) Int. Cl.
*G05B 19/18* (2006.01)
*G06F 19/00* (2006.01)
*A61B 5/04* (2006.01)
*B23K 31/02* (2006.01)

(52) U.S. Cl. .................... 700/56; 600/383; 606/129; 606/130

(58) Field of Classification Search ............. 700/56–66; 600/382, 383, 386; 606/129, 130
See application file for complete search history.

(56) References Cited

U.S. PATENT DOCUMENTS

| 3,855,442 A | | 12/1974 | Check et al. |
| 4,100,396 A | | 7/1978 | Martin |
| 4,578,168 A | | 3/1986 | Hofmann |
| 4,608,977 A | * | 9/1986 | Brown ........................ 606/130 |
| 4,638,798 A | * | 1/1987 | Shelden et al. .............. 606/130 |
| 4,670,635 A | | 6/1987 | Johnson et al. |

(Continued)

FOREIGN PATENT DOCUMENTS

JP          63306829          12/1988

*Primary Examiner*—M. N. Von Buhr
(74) *Attorney, Agent, or Firm*—Paul D. Bianco; Martin Fleit; Fleit Gibbons Gutman Bongini & Bianco PL (57) ABSTRACT

The present invention disclose a device for electrode positioning. The electrodes are preferably positioned in the XYZ planes for collecting and recording the signals of the cell activity. This activity is afterwards amplified, filtered, sorted and acquired into an acquisition system like a computer memory.

The electrode positioning device according to the present invention enable any configuration of electrode positioning. The device is comprised of: a base which is mounted onto the head directly or indirectly using a remote adapter, movable terminal holders which are mounted on said base directly or indirectly, extend guides which are mounted on said movable terminal holders and movable electrode holders which are mounted on said extended guides. The electrodes are actuated by suitable actuating means. The terminals may be connected to the terminal holder by a ball joint or a hinge.

16 Claims, 11 Drawing Sheets

U.S. PATENT DOCUMENTS

| | | | |
|---|---|---|---|
| 4,706,665 A * | 11/1987 | Gouda | 606/130 |
| 5,331,970 A * | 7/1994 | Gevins et al. | 600/544 |
| 5,518,007 A * | 5/1996 | Becker | 600/390 |
| 5,649,936 A * | 7/1997 | Real | 606/130 |
| 5,817,029 A * | 10/1998 | Gevins et al. | 600/544 |
| 5,817,106 A * | 10/1998 | Real | 606/130 |
| 5,891,034 A * | 4/1999 | Bucholz | 600/426 |
| 5,891,157 A * | 4/1999 | Day et al. | 606/130 |
| 5,928,143 A * | 7/1999 | McNaughton | 600/373 |
| 6,106,203 A | 8/2000 | Asmis et al. | |
| 6,110,182 A * | 8/2000 | Mowlai-Ashtiani | 606/130 |
| 6,148,742 A | 11/2000 | Conatable et al. | |
| 6,258,103 B1 * | 7/2001 | Saracione | 606/130 |
| 6,353,199 B1 | 3/2002 | Hosaka et al. | |
| 6,413,263 B1 * | 7/2002 | Lobdill et al. | 606/129 |
| 6,416,520 B1 * | 7/2002 | Kynast et al. | 606/130 |
| 6,423,077 B2 * | 7/2002 | Carol et al. | 606/130 |
| 6,470,226 B1 | 10/2002 | Olesen et al. | |
| 6,556,869 B1 | 4/2003 | Leonard et al. | |
| 6,609,020 B2 | 8/2003 | Gill | |
| 6,716,220 B2 * | 4/2004 | Saracione | 606/130 |
| 6,782,288 B2 * | 8/2004 | Truwit et al. | 600/429 |
| 6,799,074 B1 * | 9/2004 | Thomas et al. | 607/116 |
| 6,902,569 B2 * | 6/2005 | Parmer et al. | 606/108 |
| 7,033,326 B1 * | 4/2006 | Pianca et al. | 600/585 |
| 7,155,316 B2 * | 12/2006 | Sutherland et al. | 700/248 |
| 7,166,113 B2 * | 1/2007 | Arambula et al. | 606/130 |
| 7,217,276 B2 * | 5/2007 | Henderson et al. | 606/130 |
| 7,235,084 B2 * | 6/2007 | Skakoon et al. | 606/130 |

* cited by examiner

ELECTRODE POSITIONING DEVICE FOR THREE-AXES INDEPENDENT ELECTRODE POSITIONING

This Application is the National Stage of International Application No. PCT/IL 03/00679 filed Aug. 17, 2003, which claims the benefit of Israeli Application No. 151,315 filed Aug. 18, 2002.

BACKGROUND OF THE INVENTION

The present invention relates to a device for electrode (as herein defined) positioning for extra cellular recording (hereafter called "electrode positioning device") of cell activity of the brain and of the nervous system of a human or an animal body, (hereinafter called "brain"). The electrodes are preferably positioned in the XYZ planes for collecting and recording the signals of the cell activity. This activity is afterwards amplified, filtered, sorted and acquired into an acquisition system like a computer memory.

The positioning of the electrodes is important for reaching a specific target in the brain for diagnostic, research and even healing purposes, e.g. for extra cellular recording from the brain and the nervous system as well as in functional neurosurgery. Such electrode positioning devices are known. They consist essentially of a base or an adapter, for positioning the electrodes in the XY plane as well as in a system for positioning them in the Z plane (mounted upon same in a stable manner and connecting means both to the brain and to the signal recording device). This device is mechanically connected so that it can reach the target in the brain from one end and connected to the signal conditioning system on the other end.

There are known many such devices. Most of them have many advantages. However all the known devices have two main disadvantages which make them unsatisfactory in the use thereof. Such devices are, for example:

1. The Alpha Omega System—EPS
2. The Thomas Recording System—Eckhorn
3. The FHC System—Micro Step Multi Drive system All these systems have the following disadvantages:
The positioning of the electrodes individually in the XY plane is very complicated and expensive. For each layout of the electrodes a special device is needed with a suitable layout of holes.
The number of channels/electrodes that can be effectively used at once is limited to 32 or less.

It has thus been desirable to develop an electrode positioning device which does not have said disadvantages. Said device should be easy to manufacture and use and not be too expensive.

SUMMARY OF THE INVENTION

The present invention thus includes in an electrode positioning device (as herein defined) which includes in a base which is to be connected to the brain directly or indirectly using a remote adapter, on said base being mounted directly or indirectly movable terminal holders on which holders extend guides, on which guides extend movable means which means hold the guiding tubes (as well called tubes) and the electrodes, said electrodes being actuated by suitable actuating means.

The movable means may be conveyor, tubes and the like.

The base may sit on a chamber, a stereotactic frame, a robot's arm or any other suitable adaptation arrangement. The base may be round, rectangular, arc or have any other suitable geometry, but the round shape is preferred. The base may comprise a groove or any other suitable arrangement for adapting a moving cartridge that comprises the terminal holder or the groove or the suitable arrangement may comprise the terminal holder without using a cartridge.

In the device according to the present invention, the user works preferably with a multi-channel system with the possibility to position each electrode or group of electrodes in the XYZ planes individually and independently.

A chamber or well, if present, may be a part of the device according to the present invention, or the device may also be connected by a remote adapter to the brain.

The electrode in connection with the present invention may be a microelectrode or macro-electrode etc. However, the electrode in connection with the present invention may be a probe, an injection needle or any other suitable component that may be used with the system. The Electrode Guiding tube is preferably made in a special manner, i.e. with a bend feature in order to enable the electrodes/probes to get near each other. More than one electrode may be inserted into a tube in order to increase the number of channels. More than one tube is advantageously mounted in the same terminal.

As indicated above, in an advantageous embodiment of the present invention a base with a special geometry is designed. A cartridge is preferably located within a groove or in any other suitable form in the base. This cartridge comprises the terminal holder, which holder may move inside the channel toward the center of the base and backward, while the cartridge moves around the center of the base. These moves enable the user to take the electrodes to any required position within the working range.

When the maximum number of terminals is used the cartridge can no longer move because there is no place for such movement. In this case the cartridge is canceled and the base itself is made to accommodate the terminal holders.

All required layouts of the electrodes can be reached because the terminal can move toward the center and backward and also be rotated around its center and around the center of the base. The holders of the electrodes and of the tubes do not prevent the tubes to get near each other because the outer tubes (The Electrode Guiding tube) are advantageously bent.

The terminal may be connected to the base terminal holder by a ball joint.

The terminal may be made round or rectangular. It advantageously includes two holders inside it. Each holder includes a thread and is screwed to a threaded rod inside the tube. The holders may have a special geometry. One holder holds the guiding tube (tubing holder)—and moves it up and down. The second holder holds the electrode (electrode holder) and moves it up and down. Each holder moves up and down when rotating the threaded rod that is connected to it. In order to enable to have one terminal for both holders, the terminal should accommodate two screws therefore each holder preferably includes two holes one threaded and one simple. Opposite the simple hole in one holder there is a threaded hole in the second holder. The terminal may be rotated around its axes in order to achieve extra flexibility in the XY positioning. The terminal is preferably installed on the terminal holder by closing a lock knob or by a ball joint or any other adapting mean. The terminal itself may be mounted on a stereotactic frame or other suitable adaptation arrangement and may be used as an independent system by attaching the proper adaptation arrangement to its base. Additional way to move the holders as a replacement for the threaded rods could be a telescopic tube or a hydraulic piston. Or other pushing mean.

The terminals may be arranged in various positions, each being distanced differently from the center of the base and individually being located in the XYZ plane.

The actuating means in the Z direction may be electrical ones, e.g. a motor; hydraulic ones and even manual ones.

The moment the electrical or hydraulic means for actuating in the Z direction, are no longer required, they may be removed and the device may be covered by a suitable cover. This possibility is also within the scope of the present invention.

BRIEF DESCRIPTION OF THE DRAWINGS

These and further features and advantages of the invention will become more clearly understood in the light of the ensuing description of a preferred embodiment thereof, given by way of example only, with reference to the accompanying drawings, wherein.

DETAILED DESCRIPTION OF THE PREFERRED EMBODIMENTS

Figure 1:
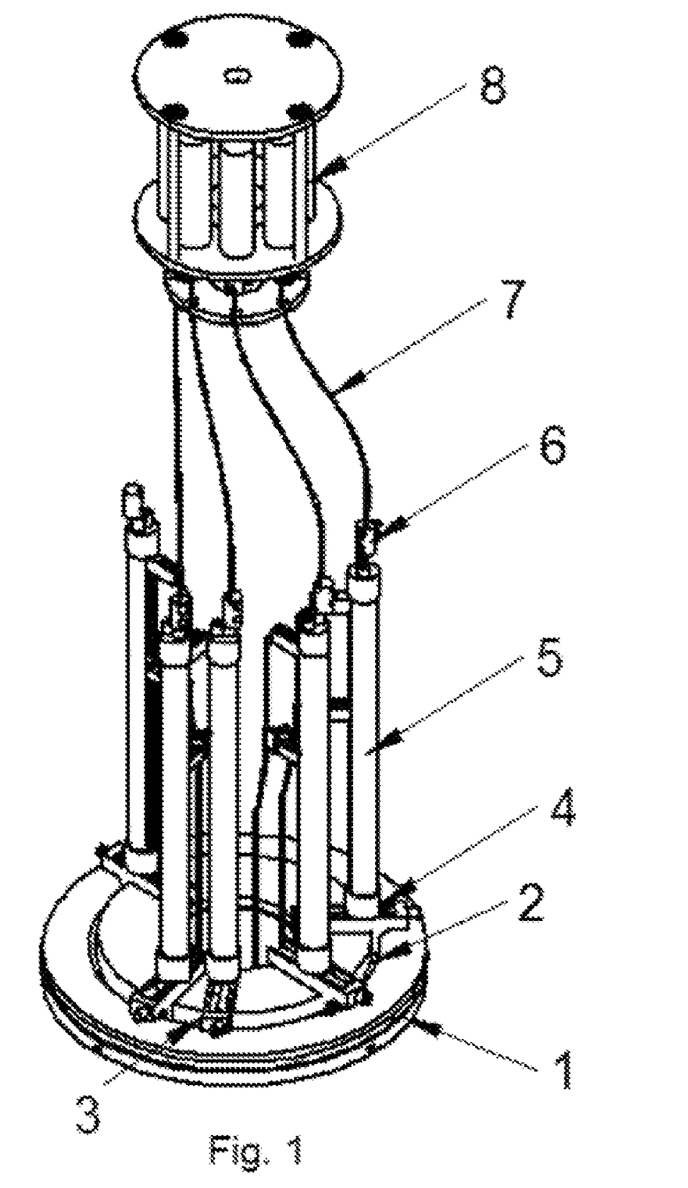
FIG. 1 shows a perspective view of the device according to the present invention.

FIG. 1 comprises base 1, groove 2, in which move cartridges 3. On the cartridge 3 is mounted terminal holder 4 which holds terminal 5, in which extend electrode holder 11 and tube holder 17. To the other end of terminal holders 5 are connected by way of shaft connector 6, shafts (cables) 7 which in turn are connected to engine 8 (for the sake of clarity there are referenced only one, cartridge 3, terminal holder 4, screw 6 and cable 7). Terminal holders 4 may move forward and backward in cartridges 3, which cartridge 3 in turn may move in groove 2 and around base 1. FIG. 1 shows a device with only 5 terminals by way of example. It is connected to the motor with a remote control shaft 7 The motor and shafts may be removed in order to install a cover. A system without the motors and shafts may be used as a manual system.

Figure 2:
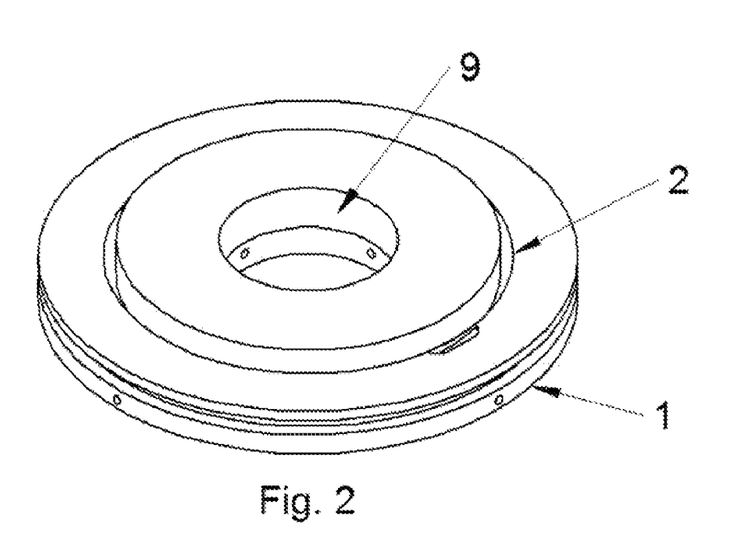
FIG. 2 shows a perspective view of a base being part of the device shown in FIG. 1.

FIG. 2 shows base 1 comprising groove 2 having an opening 9 to be mounted on the chamber 10 or other mechanical adaptation arrangement. (not shown).

Figure 3:
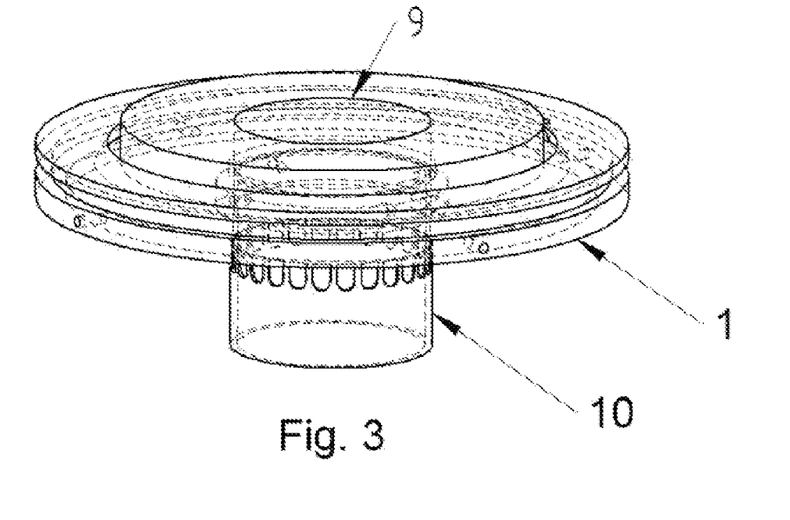
FIG. 3 shows a perspective view of the base shown in FIG. 2 connected to a chamber which is in turn connected to a brain.

FIG. 3 shows base 1 shown in FIG. 2 sitting on chamber 10 mounted on opening 9. Chamber 10 sits on the brain or on another mechanical adaptation arrangement.

Figure 4:
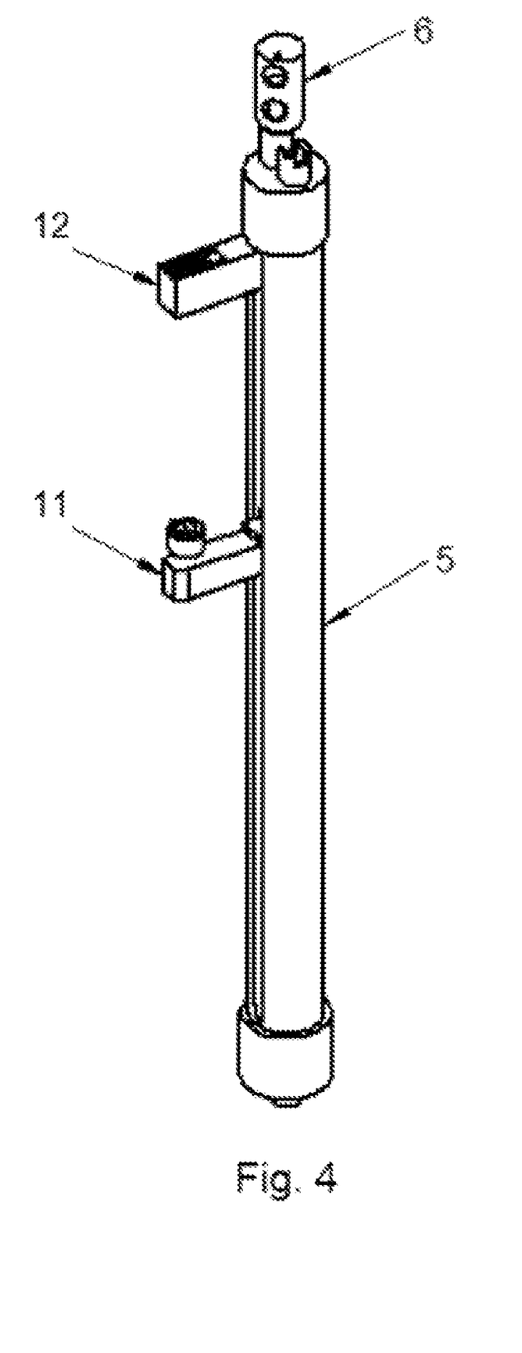
FIG. 4 shows a perspective view of a terminal.

FIG. 4 shows a detail of terminal 5 comprising tube holder 11 and electrode holder 12. Said terminal 5 is mounted on a terminal holder 4 (not shown)—and terminates with shaft connector 6.

Figure 5:
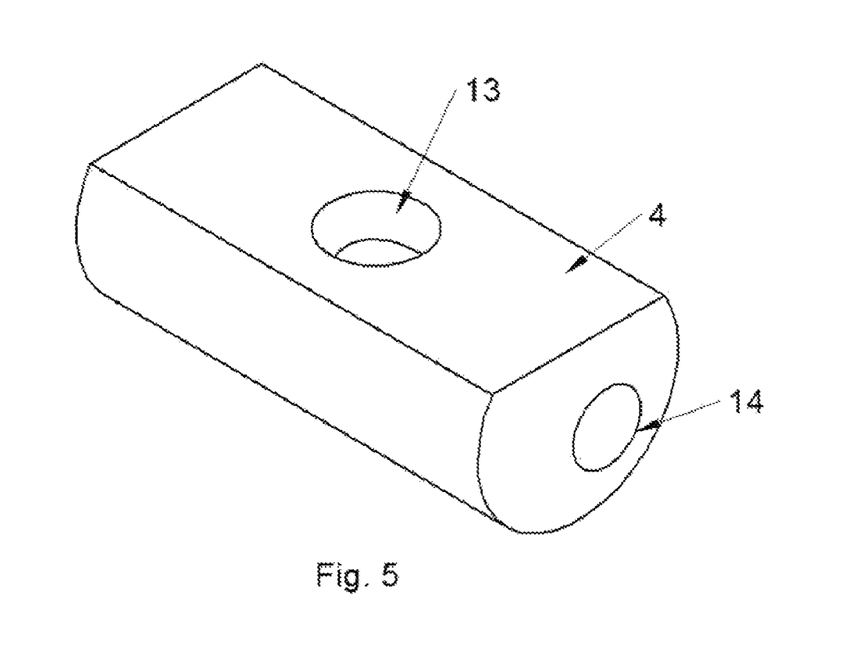
FIG. 5 shows a perspective view of a terminal holder.

FIG. 5 shows a terminal holder comprising holes 13 and 14. Hole 13 is connected to a lock knob that locks terminal 5 and hole 14 is connected to a screw that moves the terminal holder toward the center of the base and backward.

Figure 6:
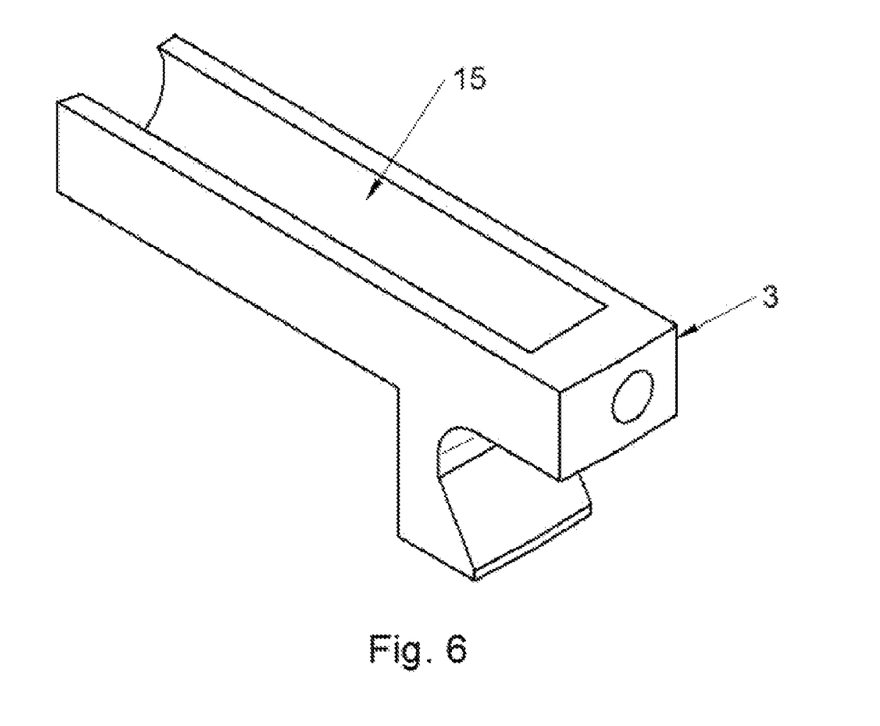
FIG. 6 shows a perspective view of a cartridge.

FIG. 6 shows cartridge 3 in which is seen channel 15 in which terminal holder 4 can move.

Figure 7:
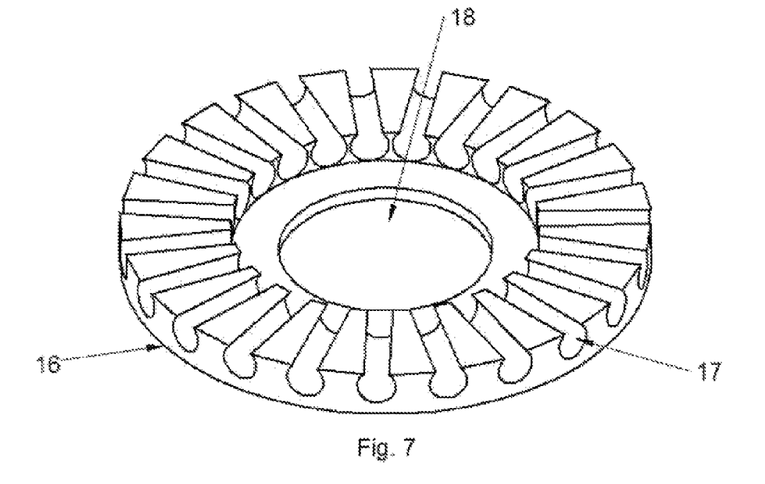
FIG. 7 shows a perspective view of a base being part of another embodiment of the device according to the present invention which base does not comprise any cartridge.

FIG. 7 shows base 16 in which are located channels 17 and opening 18. In channels 17 can move terminal holders 4 forward and backward. Opening 18 is sitting on the brain or a chamber or a mechanical adaptation arrangement (not shown).

Figure 8:
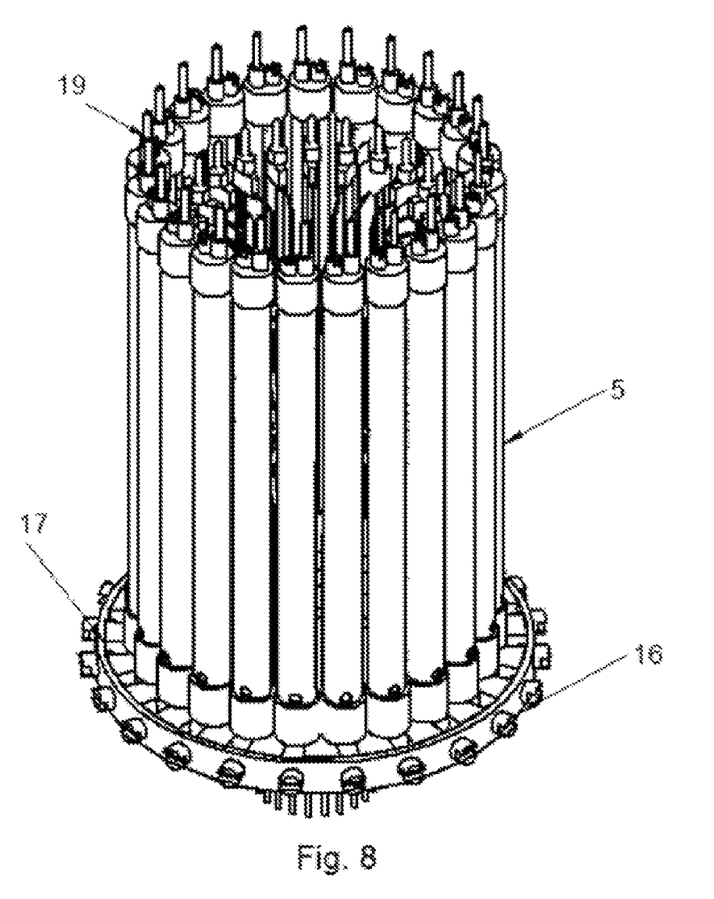
FIG. 8 shows a perspective view of a device having a base according to FIG. 7.

FIG. 8 shows another perspective view of the embodiment of the present invention which does not comprise any cartridge. This embodiment includes base 16, channels 17 (not seen clearly), terminals 5 and screws 19.

Figure 9:
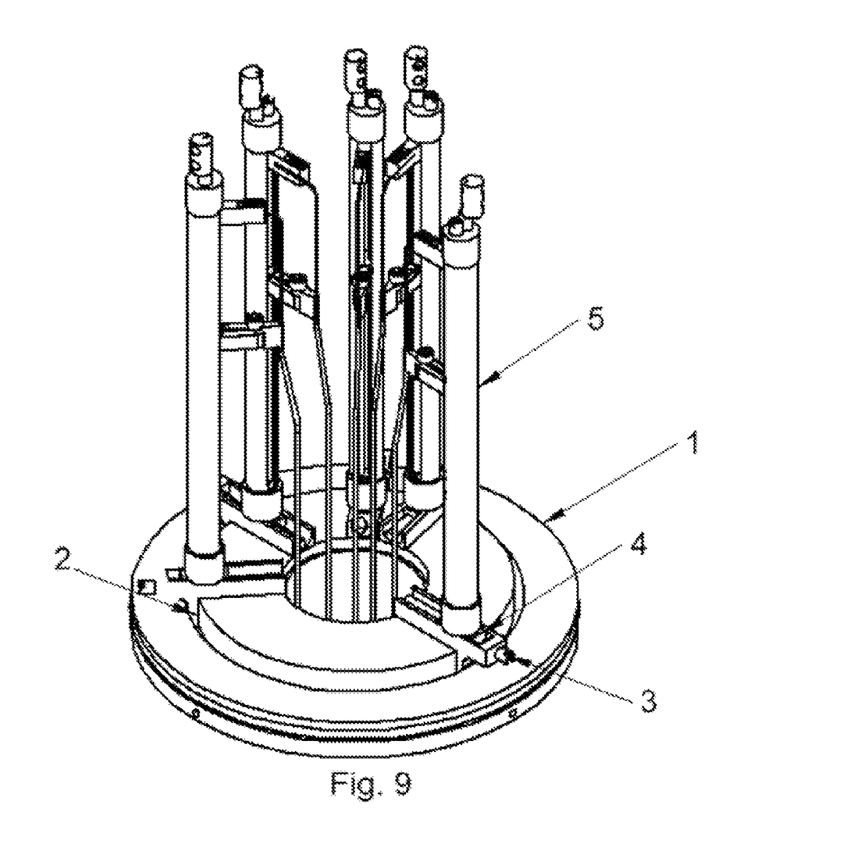
FIG. 9 shows a perspective view of a manual device according to the present invention in which the electrodes are positioned in various distances from the center.

FIG. 9 shows a device in which terminals 5 can move with terminal holder 4 on cartridge 3 which can move in groove 2 around the center of base 1.

Figure 10:
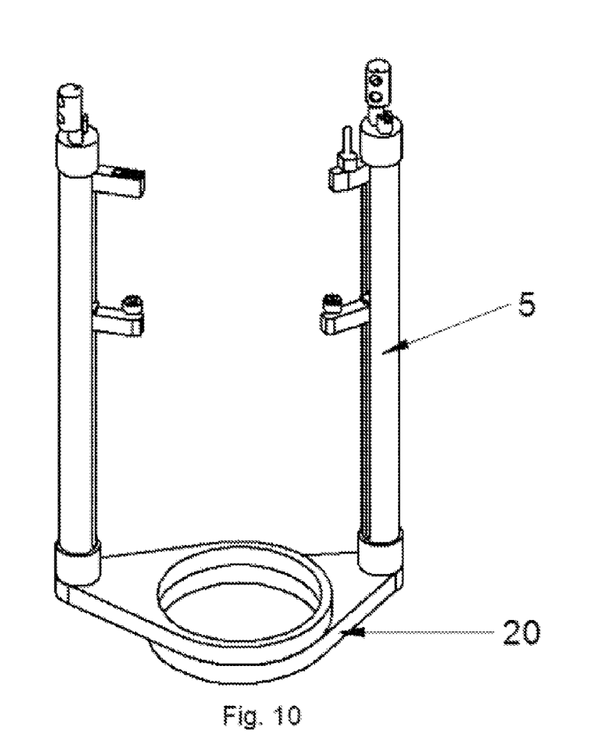
FIG. 10 shows a perspective view of a device where the terminals are independently used and adapted on a special adaptation arrangement.

FIG. 10 shows terminal 5 with special adaptation 20 which may be adapted on a chamber or stereotactic frame or other adaptation (not shown).

Figure 11:
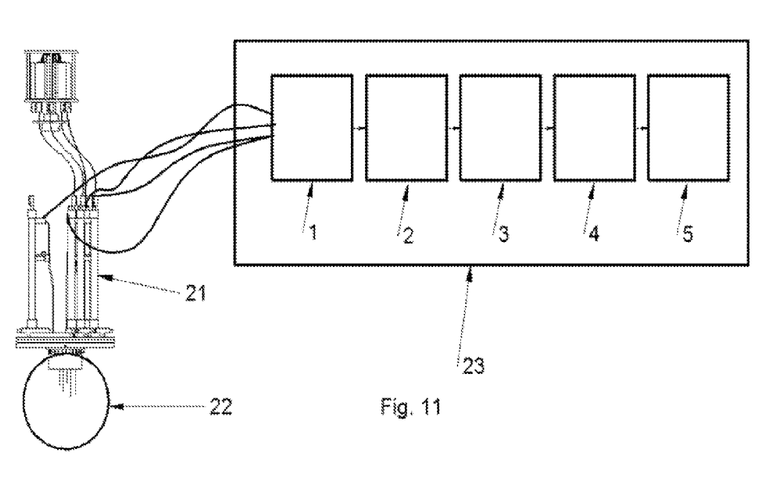
FIG. 11 shows a schematic view of an electric signal transmitting device according to the present invention being connected at one end to the brain and at the second end to a device for recording cell activity.

FIG. 11 describes the different stages in the micro recording procedure of brain activity. In this procedure the user inserts electrodes into the brain and records cell activity.

The first system in the setup is the electrode manipulator. This manipulator sits on the brain (in some cases it does not sit on the brain but it is holed away from it). The procedure is performed in the following stages:

Stage #1: Head stage—amplifier for first stage amplification of the signal.

Stage #2: signal conditioning—further amplification and filtering of the signal.

Stage #3: spike sorting—the spikes are sorted according to shape, amplitude or other specifications. This sorting could be done in real time during the recording procedure or it also could be done after the experiment.

Stage #4: Data acquisition—in this stage the signal is acquired for post processing.

Stage #5: Post processing—in addition to the spike sorting in stage #3, a finer sorting could be done.

The schematic view shown in FIG. 11 shows device 21 according to the present invention being connected at one end to brain 22 and on the other hand to micro-recording device 23.

What is claimed is:

1. An electrode positioning device, comprising:
   electrodes that are actuated by actuating means;
   a base which is mounted onto a head using a remote adapter;
   movable terminal holders which are mounted on said base directly or indirectly;
   terminals which are mounted on said movable terminal holders; and
   movable electrode holders which are mounted on said terminals;
   wherein said terminal holders and electrode holders enable individual and independent movement of each electrode along x, y and z axes.

2. A device according to claim 1, wherein the base is round.

3. A device according to claim 1, wherein the base is comprised of at least one groove on which the movable terminal holders are adjusted.

4. A device according to claim 1, comprising a chamber, wherein said base sits on said chamber.

5. A device according to claim 1, wherein the electrode is bent.

6. A device according to claim 1, wherein the electrode guides are bent.

7. A device according to claim 1, wherein each terminal comprises more than one tube.

8. A device according to claim 1, wherein each tube comprises more than one electrode.

9. A device according to claim 1, wherein each terminal comprises more than one electrode.

10. A device according to claim 1, wherein each terminal holds two holders, each holder including two holes, one threaded and one simple.

11. A device according to claim 1, wherein the terminals are arranged in different distances from the center of the base.

12. A device according to claim 1, wherein said activating means are one of: electrical, hydraulic or manual.

13. A device according to claim 1, wherein the guides are at least one of tubes, or rods.

14. A device according to claim 1, wherein the actuators are removed and are substituted by a cover.

15. A device according to claim 1, wherein said electrode is held within a guiding tube.

16. A device according to claim 1 wherein the electrodes are at least one of probes or needles.

* * * * *